US009445731B2

United States Patent
Fukuzawa et al.

(10) Patent No.: US 9,445,731 B2
(45) Date of Patent: Sep. 20, 2016

(54) PULSE WAVE VELOCITY MEASURING DEVICE AND PULSE WAVE VELOCITY MEASUREMENT METHOD

(75) Inventors: Hideaki Fukuzawa, Kanagawa-ken (JP); Osamu Nishimura, Kanagawa-ken (JP); Takehiko Suzuki, Kanagawa-ken (JP); Michiko Hara, Kanagawa-ken (JP); Yoshihiko Fuji, Kanagawa-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 775 days.

(21) Appl. No.: 13/468,511

(22) Filed: May 10, 2012

(65) Prior Publication Data

US 2013/0079648 A1    Mar. 28, 2013

(30) Foreign Application Priority Data

Sep. 27, 2011  (JP) .................................. 2011-210317

(51) Int. Cl.
  *A61B 5/02*  (2006.01)
  *A61B 5/021*  (2006.01)
  *A61B 5/00*  (2006.01)

(52) U.S. Cl.
  CPC ....... A61B 5/02141 (2013.01); A61B 5/02125 (2013.01); *A61B 5/6832* (2013.01); *A61B 2562/0223* (2013.01)

(58) Field of Classification Search
  CPC ...................................... A61B 5/021
  USPC ...................................... 600/500
  See application file for complete search history.

(56) References Cited

U.S. PATENT DOCUMENTS

| 5,243,992 A * | 9/1993 | Eckerle et al. ............... 600/503 |
| 5,309,916 A * | 5/1994 | Hatschek ....................... 600/485 |
| 2002/0107450 A1* | 8/2002 | Ogura ........................... 600/490 |
| 2006/0211942 A1* | 9/2006 | Hoctor ............... A61B 5/02125 |
| | | 600/438 |

(Continued)

FOREIGN PATENT DOCUMENTS

| JP | 3-146027 A | 6/1991 |
| JP | 2001-161650 A | 6/2001 |

(Continued)

OTHER PUBLICATIONS

"High-Sensitivity InSb Thin-Film Micro-Hall Sensor Arrays for Simultaneous Multiple Detection of Magnetic Beads for Biomedical Applications" by Togawa et al., vol. 41, No. 10, pp. 3661-3663, 2005.*

(Continued)

*Primary Examiner* — Patricia Mallari
*Assistant Examiner* — Vasuda Ramachandran
(74) *Attorney, Agent, or Firm* — Oblon, McClelland, Maier & Neustadt, L.L.P.

(57) ABSTRACT

According to one embodiment, a pulse wave velocity measuring device includes a first sensor, a second sensor, a base body and a calculation unit. The first sensor is configured to sense a pulse wave propagating through an interior of a vessel. The second sensor is separated from the first sensor and is configured to sense the pulse wave. The base body is configured to hold the first sensor and the second sensor and regulate a distance between the first sensor and the second sensor. The calculation unit is configured to derive a difference between a time of the sensing of the pulse wave by the first sensor and a time of the sensing of the pulse wave by the second sensor.

12 Claims, 8 Drawing Sheets

(56) References Cited

U.S. PATENT DOCUMENTS

| | | |
|---|---|---|
| 2007/0118040 A1* | 5/2007 | Lee et al. .................. 600/500 |
| 2008/0094059 A1* | 4/2008 | Sasaki et al. .......... G01R 33/18 324/252 |
| 2010/0228139 A1 | 9/2010 | Nanba et al. |

FOREIGN PATENT DOCUMENTS

| | | |
|---|---|---|
| JP | 2002-148132 A | 5/2002 |
| JP | 2003-24310 A | 1/2003 |
| JP | 2005-270544 A | 10/2005 |
| JP | 2010-207347 A | 9/2010 |

OTHER PUBLICATIONS

"Design and performance of GMR sensors for the detection of magnetic microbeads in biosensors" by Rife et al., Sensors and Actuators A, vol. 107, pp. 209-218, 2003.*

U.S. Appl. No. 13/927,886, Jun. 26, 2013, Fuji, et al.

Office Action issued Oct. 14, 2014, in Japanese Patent Application No. 2011-210317 with English translation.

* cited by examiner

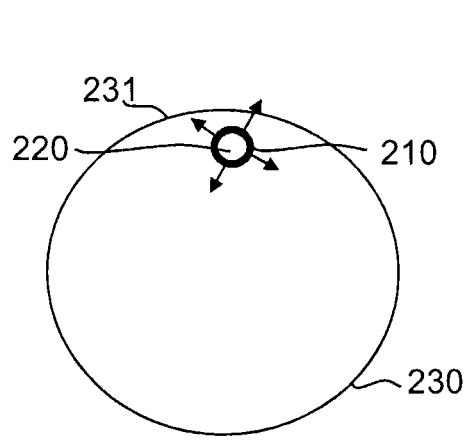
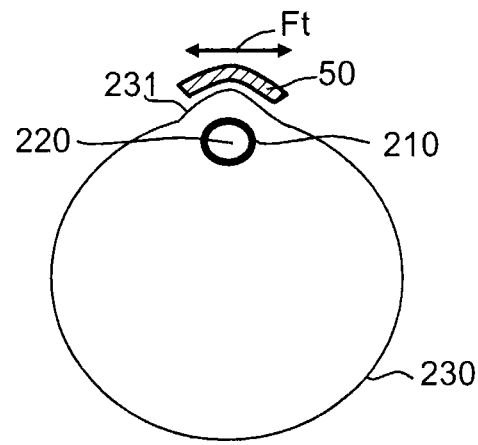
FIG. 4A　　　　　FIG. 4B
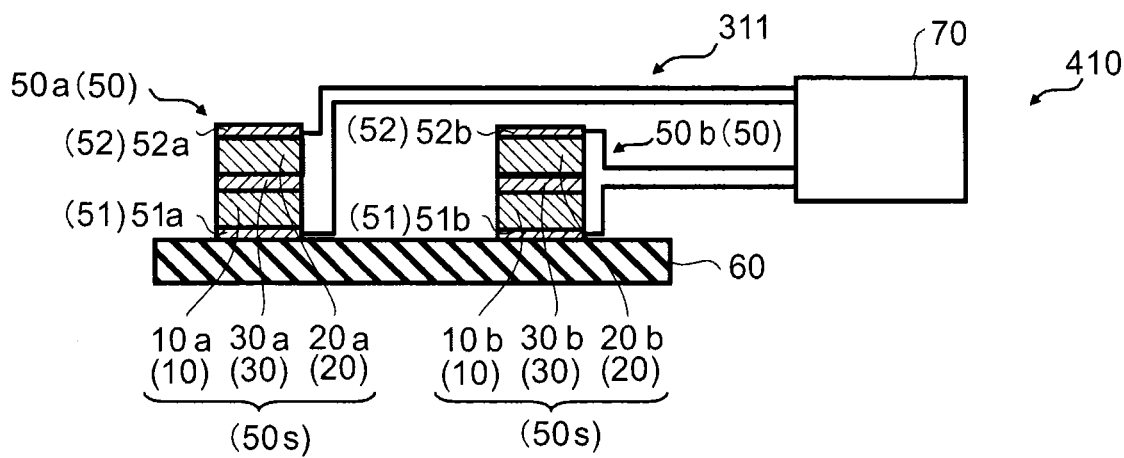
FIG. 5

US 9,445,731 B2

PULSE WAVE VELOCITY MEASURING DEVICE AND PULSE WAVE VELOCITY MEASUREMENT METHOD

CROSS-REFERENCE TO RELATED APPLICATIONS

This application is based upon and claims the benefit of priority from the prior Japanese Patent Application No. 2011-210317, filed on Sep. 27, 2011; the entire contents of which are incorporated herein by reference.

FIELD

Embodiments described herein relate generally to a pulse wave velocity measuring device and a pulse wave velocity measurement method.

BACKGROUND

To measure blood pressure and the like, for example, a measurement of pulse wave velocity (PWV) is performed. In such a method, the PWV is determined from the difference of the measurement times of the pulse wave between, for example, a measurement point proximal to the heart and a measurement point distal to the heart, e.g., the wrist or the like. In this example, complexity is felt by the examinee because wiring extends from the two greatly distal measurement points. The downsizing of the device is difficult; and continuous measurement in daily life is difficult.

BRIEF DESCRIPTION OF THE DRAWINGS

FIG. 4A and FIG. 4B are schematic cross-sectional views showing the operation of the pulse wave velocity measuring device according to the first embodiment;

FIG. 5 is a schematic view showing a pulse wave velocity measuring device according to the first embodiment;

DETAILED DESCRIPTION

Figure 1:
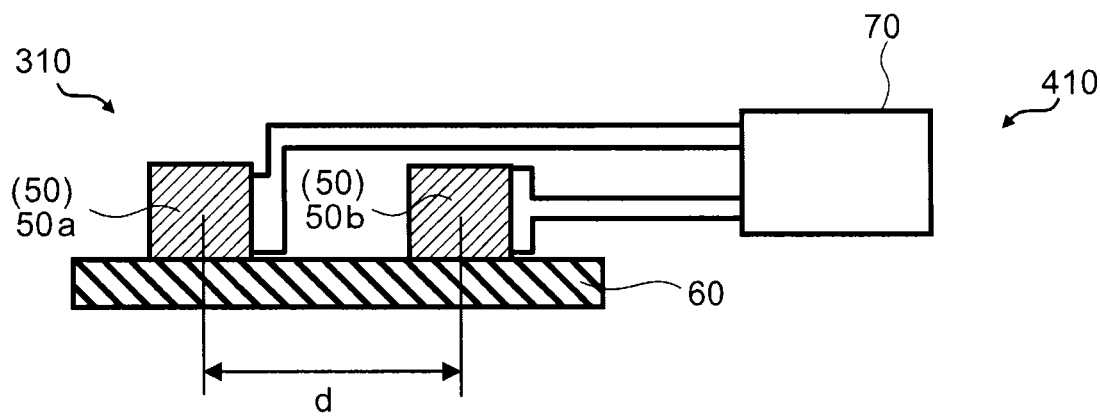
FIG. 1 is a schematic view showing a pulse wave velocity measuring device according to a first embodiment.

According to one embodiment, a pulse wave velocity measuring device includes a first sensor, a second sensor, a base body and a calculation unit. The first sensor is configured to sense a pulse wave propagating through an interior of a vessel. The second sensor is separated from the first sensor and is configured to sense the pulse wave. The base body is configured to hold the first sensor and the second sensor and regulate a distance between the first sensor and the second sensor. The calculation unit is configured to derive a difference between a time of the sensing of the pulse wave by the first sensor and a time of the sensing of the pulse wave by the second sensor.

According to another embodiment, a pulse wave velocity measurement method is disclosed. The method can include sensing a pulse wave propagating through an interior of a vessel of a sense object by causing a measurement sensor to contact the sense object. The measurement sensor includes a base body, a first sensor, and a second sensor. The pulse wave is sensed using the first sensor and the second sensor. The first sensor is held by the base body, and the second sensor is held by the base body to be separated from the first sensor. A distance between the first sensor and the second sensor is regulated by the base body. The method can include deriving a pulse wave velocity based on a difference between a time of the sensing of the pulse wave by the first sensor and a time of the sensing of the pulse wave by the second sensor.

Various embodiments will be described hereinafter with reference to the accompanying drawings.

The drawings are schematic or conceptual; and the proportions of sizes between portions and the like are not necessarily the same as the actual values thereof. The dimensions and the proportions may be illustrated differently among the drawings, even for identical portions.

In the drawings and the specification of the application, components similar to those described in regard to a drawing thereinabove are marked with like reference numerals, and a detailed description is omitted as appropriate.

First Embodiment

FIG. 1 is a schematic view illustrating the configuration of a pulse wave velocity measuring device according to a first embodiment. As shown in FIG. 1, the pulse wave velocity measuring device 410 according to the embodiment includes a first sensor 50a, a second sensor 50b, a base body 60, and a calculation unit 70.

The first sensor 50a senses a pulse wave propagating through the interior of a vessel (e.g., a blood vessel). The second sensor 50b is separated from the first sensor 50a. The second sensor 50b also senses the pulse wave. The first sensor 50a senses, for example, the strain due to the pulse wave propagating through the interior of the vessel. The second sensor 50b senses, for example, the strain due to the pulse wave.

The base body 60 holds the first sensor 50a and the second sensor 50b. The base body 60 regulates a distance d between the first sensor 50a and the second sensor 50b.

The base body 60 may include, for example, a substrate (e.g., a silicon substrate and the like) that is used when manufacturing the first sensor 50a and the second sensor 50b. The base body 60 may include, for example, a printed circuit board and the like for mounting the first sensor 50a and the second sensor 50b. The base body 60 may include a plastic substrate and the like; and the base body 60 may be flexible.

The direction from the first sensor 50a toward the second sensor 50b is taken as a first direction. For convenience in the specification of the application, the distance d between the first sensor 50a and the second sensor 50b is taken to be the distance between the center of the first sensor 50a along the first direction and the center of the second sensor 50b along the first direction.

The base body 60 holds the first sensor 50a and the second sensor 50b such that the distance d between the first sensor 50a and the second sensor 50b is substantially constant. Even in the case where the base body 60 is flexible, the base body 60 regulates the distance d between the first sensor 50a and the second sensor 50b to be substantially constant.

The first sensor 50a, the second sensor 50b, and the base body 60 are a single body. A measurement sensor 310 according to the embodiment includes the first sensor 50a, the second sensor 50b, and the base body 60.

The measurement sensor 310 according to the embodiment includes: the first sensor 50a configured to sense the strain due to the pulse wave propagating through the interior of the vessel; the second sensor 50b separated from the first sensor 50a and configured to sense the strain due to the pulse wave; and the base body 60 configured to hold the first sensor 50a and the second sensor 50b and regulate the distance between the first sensor 50a and the second sensor 50b.

To simplify the description, there are cases where the first sensor 50a and the second sensor 50b together are called the sensor 50.

The calculation unit 70 derives the difference between the time of the sensing of the pulse wave by the first sensor 50a and the time of the sensing of the pulse wave by the second sensor 50b.

In the embodiment, not less than two sensors 50 are provided in one base body 60. Therefore, the pulse wave is detected at substantially one location. According to the embodiment, a pulse wave velocity measuring device that can measure the pulse wave velocity in a local measurement range can be provided.

The distance d is not less than 1 mm and not more than 5 cm. It is more favorable for the distance d to be not less than 5 mm and not more than 2 cm. This is because such a small size is favorable for handling as substantially a single body during the measurement.

Figure 2:
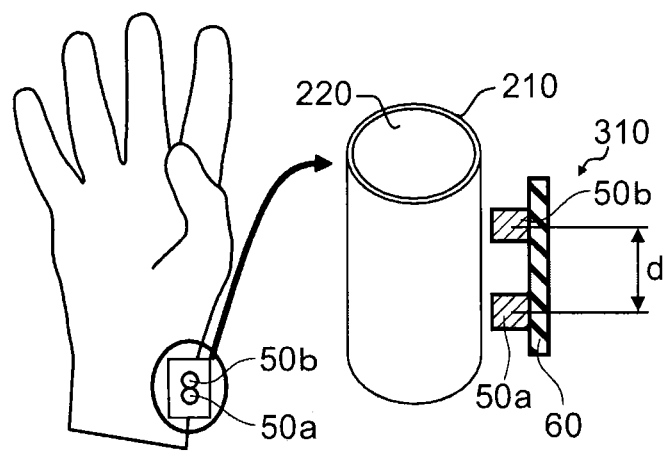
FIG. 2 is a schematic view showing a state of use of the pulse wave velocity measuring device according to the first embodiment.

FIG. 2 is a schematic view illustrating a state of use of the pulse wave velocity measuring device according to the first embodiment.

Although the measurement sensor 310 is illustrated in FIG. 2, the calculation unit 70 is not illustrated.

As shown in FIG. 2, for example, the measurement sensor 310 is mounted in contact with a wrist. The first sensor 50a and the second sensor 50b are disposed to oppose an arterial vessel 210 (a vessel) of the wrist. Blood 220 (a liquid) flows inside the arterial vessel 210. The flow of the blood 220 is a flow due to the pulse wave.

By setting the distance d to be small (e.g., not more than 5 cm), the pulse wave can be detected at substantially one measurement point.

The measurement sensor 310 may be disposed not only at the wrist but also at various positions. For example, the measurement sensor 310 may be disposed at a blood pressure measurement site. For example, the measurement sensor 310 may be adhered to the skin surface by, for example, an adhesive and the like. The measurement sensor 310 is disposed on the skin in contact with the skin. For example, the measurement sensor 310 is disposed on the skin where the arterial vessel 210 exists proximally to the surface of the skin. For example, the site where the measurement sensor 310 is disposed is a site where the pulsatory motion can be sensed from the surface of the body of the examinee.

This site (and the artery under the body surface) may be, for example, as follows: the medial bicipital groove (the brachial artery), between the flexor carpi radialis tendon and the brachioradialis tendon at the outer lower end of the forearm (the radial artery), between the flexor carpi ulnaris tendon and the superficial digital flexor tendon at the inner lower end of the forearm (the ulnar artery), the ulnar side of the extensor pollicis longus tendon (the first dorsal metacarpal artery), the axilla (the axillary artery), the femoral triangle (the femoral artery), the outer side of the tibialis anterior tendon at the lower portion of the anterior surface of the leg (the anterior tibial artery), the posterior lower portion of the medial malleolus (the posterior tibial artery), the outer side of the extensor pollicis longus tendon (the dorsalis pedis artery), the carotid artery triangle (the common carotid artery), in front of the masseter insertion (the facial artery), behind the sternocleidomastoid insertion between the trapezius muscle origin and the sternocleidomastoid insertion (the lateral occipital artery), and in front of the external acoustic opening (the superficial temporal artery). The measurement sensor 310 is disposed, for example, at such a site.

Conversely, in a conventional measurement of the PWV, for example, a measurement point proximal to the heart and a measurement point distal to the heart, e.g., the wrist or the like, are used. Therefore, there is complexity; and downsizing of the device is difficult. Also, continuous measurement in daily life is difficult. Although the blood pressure is calculated by modeling the blood vessel, the blood vessels at two points such as the heart and the arm cannot actually be handled using a single model. Therefore, the measurement error is large. For example, the error is about 10 mm Hg.

Thus, the inventor of the application focused on the low measurement accuracy and the difficulty due to the complexity of using measurements at two greatly distal measurement points. The measurement of the PWV with high accuracy at a measurement location that feels like substantially one point to a human was discovered as a new problem.

In the embodiment, the measurement is performed not at two greatly distal measurement points but in a local measurement range. The complexity felt by the examinee can be markedly reduced because the pulse wave velocity can be measured in the local measurement range. Also, the device can be downsized. Further, continuous measurement in daily life is easy. Then, by being a local measurement, the blood vessel can be handled by a single model; and high measurement accuracy is obtained.

Figure 3:
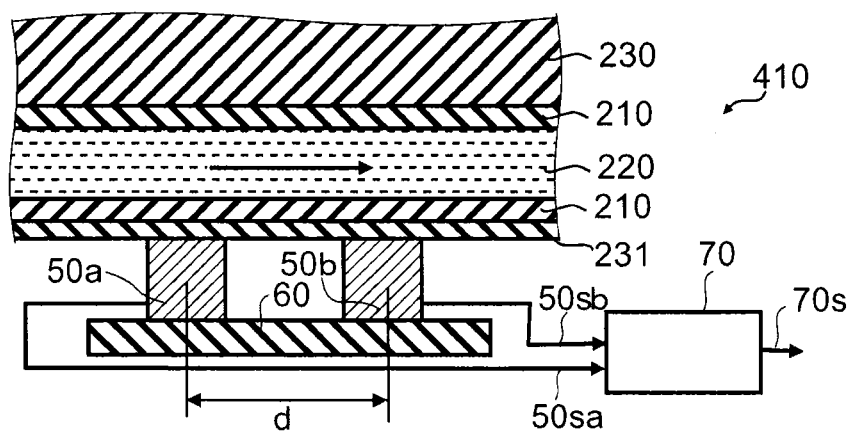
FIG. 3 is a schematic view showing the state of use of the pulse wave velocity measuring device according to the first embodiment.

FIG. 3 is a schematic view illustrating the state of use of the pulse wave velocity measuring device according to the first embodiment.

As shown in FIG. 3, the arterial vessel 210 is under the skin 231 of the body 230 of the examinee. The blood 220 flows through the arterial vessel 210. The pulse wave of the arterial vessel 210 is sensed by the first sensor 50a and the second sensor 50b that are disposed locally. The sensed signal (a first signal 50sa) of the pulse wave of the first sensor 50a and the sensed signal (a second signal 50sb) of the pulse wave of the second sensor 50b are supplied to the calculation unit 70. The calculation unit 70 derives the difference between the time of the sensing of the pulse wave by the first sensor 50a and the time of the sensing of the pulse wave by the second sensor 50b based on these signals. In the calculation unit 70, the PWV can be determined from the distance d and the difference of the times. The calculation unit 70 outputs an operation result 70s (e.g., at least one selected from the PWV and the difference of the times).

According to the pulse wave velocity measuring device 410, a pulse wave velocity can be measured in a local measurement range.

The calculation unit 70 is connected to the first sensor 50a and the second sensor 50b by, for example, wired or wireless communication (including communication by a radio signal or an optical signal). For example, the first signal 50sa of the first sensor 50a and the second signal 50sb of the second sensor 50b may be supplied to the calculation unit 70 by interconnects and the like. Or, for example, a wireless transmitting circuit may be provided on the base body 60; and the first signal 50sa and the second signal 50sb may be supplied to the calculation unit 70 by the wireless transmitting circuit.

FIG. 4A and FIG. 4B are schematic cross-sectional views illustrating an example of the operation of the pulse wave velocity measuring device according to the first embodiment.

FIG. 4A illustrates the contraction of the arterial vessel 210. FIG. 4B illustrates the state of the sensors 50 during the measurement.

As shown in FIG. 4A, the blood pressure acts by the arterial vessel 210 contracting in the diametrical direction by the blood 220 flowing through the arterial vessel 210 due to the pulse wave.

As shown in FIG. 4B, as the arterial vessel 210 expands in the diametrical direction, the skin 231 is pushed upward. At this time, tensile stress is applied to the skin 231 in a direction perpendicular to the direction in which the blood pressure acts. Simultaneously, tensile stress also acts on the sensors 50 in a constant direction.

As described below, a current is caused to flow in the sensor 50. The electrical resistance of the sensor 50 changes according to the tensile stress applied to the sensor 50. Based on this change, the pulse wave is detected by the sensor 50.

One example of the configuration of the sensor 50 and the operation of this configuration will now be described.

FIG. 5 is a schematic view illustrating the configuration of the pulse wave velocity measuring device according to the first embodiment. FIG. 5 illustrates the configuration of the cross section of a measurement sensor 311 which is one example of the measurement sensor 310 according to the embodiment.

As shown in FIG. 5, the first sensor 50a includes a first ferromagnetic layer 10a, a second ferromagnetic layer 20a, and a nonmagnetic first intermediate layer 30a provided between the first ferromagnetic layer 10a and the second ferromagnetic layer 20a. The second sensor 50b includes a third ferromagnetic layer 10b, a fourth ferromagnetic layer 20b, and a nonmagnetic second intermediate layer 30b provided between the third ferromagnetic layer 10b and the fourth ferromagnetic layer 20b.

For example, the third ferromagnetic layer 10b may include the same material as the material of the first ferromagnetic layer 10a. For example, the fourth ferromagnetic layer 20b may include the same material as the material of the second ferromagnetic layer 20a. For example, the second intermediate layer 30b may include the same material as the material of the first intermediate layer 30a. In this example, the third ferromagnetic layer 10b is in the same layer as the first ferromagnetic layer 10a. The fourth ferromagnetic layer 20b is in the same layer as the second ferromagnetic layer 20a. The second intermediate layer 30b is in the same layer as the first intermediate layer 30a.

The first sensor 50a may further include a first electrode 51a and a second electrode 52a. The first ferromagnetic layer 10a is disposed between the first electrode 51a and the second electrode 52a; and the second ferromagnetic layer 20a is disposed between the first ferromagnetic layer 10a and the second electrode 52a.

The second sensor 50b may further include a third electrode 51b and a fourth electrode 52b. The third ferromagnetic layer 10b is disposed between the third electrode 51b and the fourth electrode 52b; and the fourth ferromagnetic layer 20b is disposed between the third ferromagnetic layer 10b and the fourth electrode 52b.

To simplify the description hereinbelow, the first ferromagnetic layer 10a and the third ferromagnetic layer 10b are called the lower magnetic layer 10 for convenience. The second ferromagnetic layer 20a and the fourth ferromagnetic layer 20b are called the upper magnetic layer 20 for convenience. The first intermediate layer 30a and the second intermediate layer 30b are called the intermediate layer 30 for convenience. The lower magnetic layer 10, the intermediate layer 30, and the upper magnetic layer 20 are called the sensor stacked body 50s as appropriate. The first electrode 51a and the third electrode 51b are called the lower electrode 51 for convenience. The second electrode 52a and the fourth electrode 52b are called the upper electrode 52 for convenience.

Regarding "up" and "down" in the description recited above, the relative vertical relationship with the base body 60 is arbitrary. For example, the upper magnetic layer 20 may be disposed on the base body 60; the intermediate layer 30 may be disposed on the upper magnetic layer 20; and the lower magnetic layer 10 may be disposed on the intermediate layer 30.

In the sensor 50, for example, one selected from the lower magnetic layer 10 and the upper magnetic layer 20 is a free magnetic layer. The other selected from the lower magnetic layer 10 and the upper magnetic layer 20 is, for example, a fixed magnetic layer. However, as described below, both the lower magnetic layer 10 and the upper magnetic layer 20 may be free magnetic layers.

Hereinbelow, the example of the operation of the sensor 50 is described as the case where the lower magnetic layer 10 is a fixed magnetic layer and the upper magnetic layer 20 is a free magnetic layer. In the sensor 50, an inverse magnetostrictive effect of the ferromagnet and a MR effect arising in the sensor stacked body 50s are utilized.

The MR effect arises by the change of the relative angle of the orientation of the magnetization being read as an electrical resistance change by causing a current to flow in the sensor stacked body 50s. As described above, the tensile stress is applied to the sensor 50 by the pulse wave. When the orientation of the magnetization of the upper magnetic layer 20 (the free magnetic layer) is different from the direction of the tensile stress applied to the upper magnetic layer 20, the MR effect arises due to the inverse magnetostrictive effect. The change amount of the electrical resistance that changes due to the MR effect is the MR change amount. The value of a resistance change amount ΔR divided by a minimum resistance value R, i.e., ΔR/R, is called the MR change rate.

Figure 6A:
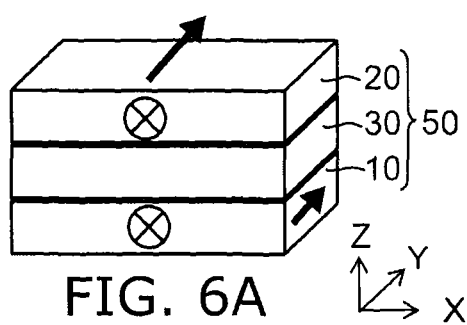
FIG. 6A to FIG. 6C are schematic perspective views showing operations of the pulse wave velocity measuring device according to the first embodiment.
Figure 6B:
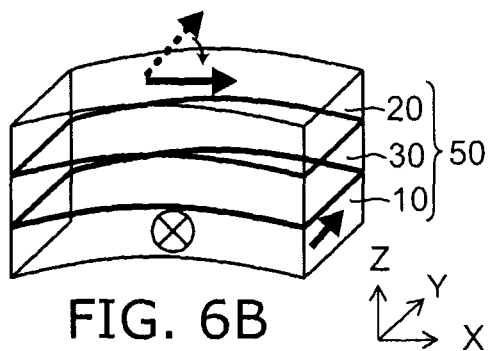
Figure 6C:
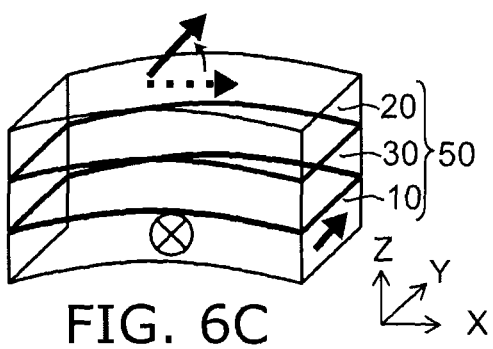

FIG. 6A to FIG. 6C are schematic perspective views illustrating operations of the pulse wave velocity measuring device according to the first embodiment.

These drawings illustrate the relationship between the direction of the magnetization and the direction of the tensile stress for the sensor stacked body 50s of the sensor 50.

FIG. 6A illustrates the state in which the tensile stress is not applied. At this time, in this example, the orientation of the magnetization of the lower magnetic layer 10 (the fixed magnetic layer) is the same as the orientation of the magnetization of the upper magnetic layer 20 (the free magnetic layer).

FIG. 6B is the state in which the tensile stress is applied. In this example, the tensile stress is applied along the X-axis direction. At this time, the magnetization of the upper magnetic layer 20 (the free magnetic layer) rotates to be in the same direction as the direction of the tensile stress. This is called the inverse magnetostrictive effect. At this time, the magnetization of the lower magnetic layer 10 (the fixed magnetic layer) is fixed. The relative angle between the orientation of the magnetization of the lower magnetic layer 10 (the fixed magnetic layer) and the orientation of the magnetization of the upper magnetic layer 20 (the free magnetic layer) changes by the magnetization of the upper magnetic layer 20 (the free magnetic layer) rotating.

In these drawings, the direction of the magnetization of the lower magnetic layer 10 (the fixed magnetic layer) is illustrated as an example; and the directions of the magnetizations may be different from the directions illustrated in these drawings.

In the inverse magnetostrictive effect, the easy magnetization axis changes according to the sign of the magnetostriction constant of the ferromagnet. In many materials having large inverse magnetostrictive effects, the magnetostriction constant has a positive sign. In the case where the magnetostriction constant has a positive sign, as described above, the direction in which the tensile stress is applied becomes the easy magnetization axis. In such a case, as recited above, the magnetization of the upper magnetic layer 20 (the free magnetic layer) rotates in the direction of the easy magnetization axis.

For example, in the case where the magnetostriction constant of the upper magnetic layer 20 (the free magnetic layer) is positive, the direction of the magnetization of the upper magnetic layer 20 (the free magnetic layer) is set to be in a direction different from the direction in which the tensile stress is applied.

On the other hand, in the case where the magnetostriction constant is negative, a direction perpendicular to the direction in which the tensile stress is applied becomes the easy magnetization axis.

FIG. 6C illustrates the state in the case where the magnetostriction constant is negative. In such a case, the direction of the magnetization of the upper magnetic layer 20 (the free magnetic layer) is set to be in a direction different from a direction perpendicular to the direction (in this example, the X-axis direction) in which the tensile stress is applied.

In these drawings, the direction of the magnetization of the lower magnetic layer 10 (the fixed magnetic layer) is illustrated as an example; and the directions of the magnetizations may be different from the directions illustrated in these drawings.

For example, the electrical resistance of the sensor stacked body 50s changes due to the MR effect according to the angle between the magnetization of the lower magnetic layer 10 and the magnetization of the upper magnetic layer 20.

Thus, the electrical resistance of the first sensor 50a and the second sensor 50b changes due to the change of the magnetization direction occurring due to the inverse magnetostrictive effect corresponding to the stress applied to the first sensor 50a and the second sensor 50b by the pulse wave.

The magnetostriction constant (λs) indicates the size of the shape deformation when the ferromagnetic layer has saturation magnetization in some direction by applying an external magnetic field. For a length L in the state in which there is no external magnetic field, the magnetostriction constant λs is ΔL/L, where the length changes an amount ΔL when the external magnetic field is applied. Although this change amount varies with the size of the external magnetic field, the magnetostriction constant λs is the value ΔL/L of the state in which a sufficient external magnetic field is applied and the magnetization is saturated.

An example of the configurations of the lower magnetic layer 10 (the first ferromagnetic layer 10a and the third ferromagnetic layer 10b), the upper magnetic layer 20 (the second ferromagnetic layer 20a and the fourth ferromagnetic layer 20b), the intermediate layer 30 (the first intermediate layer 30a and the second intermediate layer 30b), the lower electrode 51 (the first electrode 51a and the third electrode 51b), and the upper electrode 52 (the second electrode 52a and the fourth electrode 52b) will now be described.

For example, in the case where the lower magnetic layer 10 is the fixed magnetic layer, the lower magnetic layer 10 may include, for example, a CoFe alloy, a CoFeB alloy, a NiFe alloy, and the like. The thickness of the lower magnetic layer 10 is, for example, not less than 2 nanometers (nm) and not more than 6 nm.

The intermediate layer 30 may include a metal or an insulator. For example, Cu, Au, Ag, and the like may be used as the metal. In the case of being a metal, the thickness of the intermediate layer 30 is, for example, not less than 1 nm and not more than 7 nm. For example, magnesium oxide (MgO, etc.), aluminum oxide ($Al_2O_3$, etc.), titanium oxide (TiO, etc.), and zinc oxide (ZnO, etc.) may be used as the insulator. In the case of being an insulator, the thickness of the intermediate layer 30 is, for example, not less than 0.6 nm and not more than 2.5 nm.

The intermediate layer 30 may be a CCP (Current-Confined-Path) intermediate layer in which numerous nano-order metal current paths pierce a portion of the layer of an insulator such as those recited above. Specifically, a nano current path structure including Cu, Au, Ag, Ni, Fe, Co, and the like is formed in a portion of aluminum oxide ($Al_2O_3$, etc.). In such a case, the thickness of the intermediate layer 30 is, for example, not less than 1 nm and not more than 3 nm. The diameter of the nano current path is not less than 0.5 nm and not more than 10 nm. More specifically, the diameter of the nano current path is not less than 1 nm and not more than 7 nm.

In the case where the upper magnetic layer 20 is the free magnetic layer, the upper magnetic layer 20 may include, for example, an FeCo alloy, a NiFe alloy, and the like. Other than these, the second ferromagnetic layer 20a may include an Fe—Co—Si—B alloy, a Tb-M-Fe alloy with $\lambda s>100$ ppm (M being Sm, Eu, Gd, Dy, Ho, and Er), a Tb-M1-Fe-M2 alloy (M1 being Sm, Eu, Gd, Dy, Ho, and Er and M2 being Ti, Cr, Mn, Co, Cu, Nb, Mo, W, and Ta), an Fe-M3-M4-B alloy (M3 being Ti, Cr, Mn, Co, Cu, Nb, Mo, W, and Ta and M4 being Ce, Pr, Nd, Sm, Tb, Dy, and Er), Ni, Al—Fe, ferrite ($Fe_3O_4$, $(FeCo)_3O_4$), etc.) and the like. The thickness of the upper magnetic layer 20 is, for example, not less than 2 nm.

The upper magnetic layer 20 may have a two-layer structure. In such a case, the upper magnetic layer 20 may include a layer of an FeCo alloy or one of the following layers stacked with a layer of an FeCo alloy. A layer of a material selected from an Fe—Co—Si—B alloy, a Tb-M-Fe alloy with $\lambda s>100$ ppm (M being Sm, Eu, Gd, Dy, Ho, and Er), a Tb-M1-Fe-M2 alloy (M1 being Sm, Eu, Gd, Dy, Ho, and Er and M2 being Ti, Cr, Mn, Co, Cu, Nb, Mo, W, and Ta), an Fe-M3-M4-B alloy (M3 being Ti, Cr, Mn, Co, Cu, Nb, Mo, W, and Ta and M4 being Ce, Pr, Nd, Sm, Tb, Dy, and Er), Ni, Al—Fe, ferrite ($Fe_3O_4$, $(FeCo)_3O_4$), etc.) and the like may be stacked with a layer of the FeCo alloy.

The lower electrode 51 and the upper electrode 52 may include, for example, Au, Cu, Ta, Al, and the like which are nonmagnetic bodies. By using a material that is a soft magnetic body as the lower electrode 51 and the upper electrode 52, magnetic noise from the outside which affects the sensor stacked body 50s can be reduced. For example, permalloy (a NiFe alloy) and silicon steel (an FeSi alloy) may be used as the material of the soft magnetic body. The sensor 50 is covered with an insulator such as aluminum oxide (e.g., $Al_2O_3$), silicon oxide (e.g., $SiO_2$), etc.

For example, in the case where the intermediate layer 30 is a metal, a GMR (Giant Magnetoresistance) effect arises. In the case where the intermediate layer 30 is an insulator, a TMR (Tunneling Magnetoresistance) effect arises. For example, in the sensor 50, a CPP (Current Perpendicular to Plane)-GMR effect may be used in which a current is caused to flow along, for example, the stacking direction of the sensor stacked body 50s.

Thus, in the embodiment, the inverse magnetostrictive phenomenon is used in the sensor 50. Thereby, highly sensitive detection is possible. In the case where the inverse magnetostrictive effect is used, for example, the magnetization direction of the magnetic layer of at least one selected from the lower magnetic layer 10 and the upper magnetic layer 20 changes due to the strain applied from the outside. The relative angle of the magnetization of the two magnetic layers changes due to the application/non-application of the strain from the outside. The sensor 50 functions as a strain sensor because the electrical resistance changes due to the strain applied from the outside.

In other words, the magnetization direction of the magnetic layer of at least one selected from the lower magnetic layer 10 and the upper magnetic layer 20 changes according to the stress. The absolute value of the magnetostriction constant of the magnetic layer of the at least one selected from the lower magnetic layer 10 and the upper magnetic layer 20 (the magnetic layer in which the magnetization direction changes according to the stress) is set to be, for example, not less than $10^{-5}$. Thereby, due to the inverse magnetostrictive effect, the direction of the magnetization changes according to the strain applied from the outside. For example, at least one selected from the lower magnetic layer 10 and the upper magnetic layer 20 includes a metal such as Fe, Co, Ni, etc., an alloy including such metals, and the like.

The magnetostriction constant may be set to be large by selecting the elements, the added elements, and the like that are used.

For example, an oxide such as MgO is used as the intermediate layer 30. The magnetic layer on the MgO layer generally has a positive magnetostriction constant. For example, in the case where the upper magnetic layer 20 is formed on the intermediate layer 30, a free magnetic layer having a stacked configuration of CoFeB/CoFe/NiFe is used as the upper magnetic layer 20. In the case where the NiFe layer of the uppermost layer is Ni-rich, the magnetostriction constant of the NiFe layer is negative with a greater absolute value. To suppress the cancellation of the positive magnetostriction on the oxide layer, the Ni composition of the NiFe layer of the uppermost layer is not more Ni-rich than is the standard composition of $Ni_{81}Fe_{19}$ (atomic %) of permalloy which is known as a general NiFe alloy material. Specifically, it is favorable for the proportion of the Ni of the NiFe layer of the uppermost layer to be less than 80 atomic percent (atomic %). In the case where the upper magnetic layer 20 is the free magnetic layer, it is favorable for the thickness of the upper magnetic layer 20 to be, for example, not less than 1 nm and not more than 20 nm.

In the case where the upper magnetic layer 20 is the free magnetic layer, the lower magnetic layer 10 may be a fixed magnetic layer or a free magnetic layer. In the case where the lower magnetic layer 10 is the fixed magnetic layer, the direction of the magnetization of the lower magnetic layer 10 substantially does not change even when the strain is applied from the outside. Then, the electrical resistance changes according to the angle of the relative magnetization between the lower magnetic layer 10 and the upper magnetic layer 20. The strain is sensed by the difference in the electrical resistance.

In the case where both the lower magnetic layer 10 and the upper magnetic layer 20 are free magnetic layers, for example, the magnetostriction constant of the lower magnetic layer 10 is set to be different from the magnetostriction constant of the upper magnetic layer 20.

In both the case where the lower magnetic layer 10 is the fixed magnetic layer and the case where the lower magnetic layer 10 is the free magnetic layer, it is favorable for the thickness of the lower magnetic layer 10 to be, for example, not less than 1 nm and not more than 20 nm.

For example, in the case where the lower magnetic layer 10 is the fixed magnetic layer, the lower magnetic layer 10 may include a synthetic AF structure using a stacked structure of an antiferromagnetic layer/magnetic layer/Ru layer/magnetic layer and the like. The antiferromagnetic layer may include, for example, IrMn and the like. In the case where the lower magnetic layer 10 is the fixed magnetic layer, a configuration in which a hard film is used as the lower magnetic layer 10 instead of using the antiferromagnetic layer may be applied. The hard film may include, for example, CoPt, FePt, and the like.

The sensor 50 uses the spin of the magnetic layers. The surface area which is necessary for the sensor 50 may be exceedingly small. It is sufficient for the surface area of the sensor 50 to be, for example, not more than about 50 nm by 50 nm to 50 μm by 50 μm. From the aspects of manufacturing costs and obtaining sufficient position resolution, 100 nm by 100 nm to 10 μm by 10 μm is a favorable element size.

FIG. 7A to FIG. 7D are schematic perspective views illustrating portions of pulse wave velocity measuring devices according to the first embodiment.

Figure 7A:
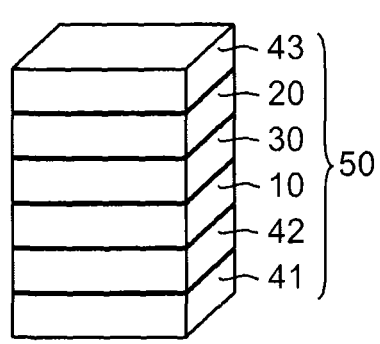
FIG. 7A to FIG. 7D are schematic perspective views showing portions of pulse wave velocity measuring devices according to the first embodiment.

In the sensor 50 in the example shown in FIG. 7A, a foundation layer 41, an antiferromagnetic layer 42, the lower magnetic layer 10 (e.g., the fixed magnetic layer), the intermediate layer 30, the upper magnetic layer 20 (e.g., the free magnetic layer), and a protective layer 43 are stacked in this order. This configuration is called, for example, a bottom-type spin-valve film.

For example, the foundation layer 41 increases the crystal orientation of the films stacked on the foundation layer 41. The foundation layer 41 may include, for example, a material having a buffering effect such as amorphous Ta and the like. For example, amorphous Ta has good adhesion with the substrate that is formed. In the foundation layer 41, Ru, NiFe, Cu, and the like that have a crystalline seed effect may be stacked on the materials having the buffering effect. The crystal orientation of the layers formed on the foundation layer 41 can be improved by using a single layer or a stacked film of these materials as the foundation layer 41. Both the wettability and the crystal orientation can be realized by employing a stacked structure of an amorphous Ta film and a crystalline film of Ru, NiFe, Cu, and the like. The thickness of the foundation layer 41 is, for example, not less than 0.5 nm and not more than 5 nm.

The protective layer 43 protects the sensor stacked body from damage when manufacturing the sensor stacked body. The protective layer 43 may include, for example, Cu, Ta, Ru, and the like or a stacked film of Cu, Ta, Ru, and the like. The thickness of the protective layer 43 is, for example, not less than 1 nm and not more than 20 nm.

Figure 7B:
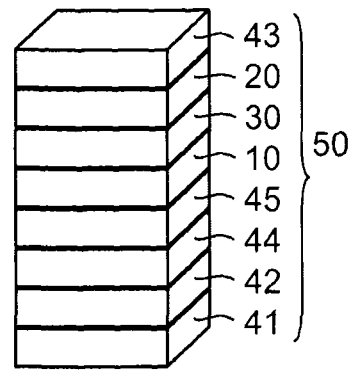

In the example shown in FIG. 7B, the foundation layer 41, the antiferromagnetic layer 42, a fixed magnetic layer 44, an antiparallel coupling layer 45, the lower magnetic layer 10 (e.g., the fixed magnetic layer), the intermediate layer 30, the upper magnetic layer 20 (e.g., the free magnetic layer), and the protective layer 43 are stacked in this order. This configuration is called, for example, a bottom-type synthetic valve film. The fixing power of the magnetization of the lower magnetic layer 10 (the fixed magnetic layer) can be increased by this configuration.

The magnetization of the fixed magnetic layer 44 is fixed in one direction by exchange coupling from the antiferromagnetic layer 42. The fixed magnetic layer 44 may include the same material as the material of the lower magnetic layer 10 (the fixed magnetic layer). The thickness of the fixed magnetic layer 44 is set to be substantially the same as the magnetic thickness (the product of the saturation magnetization and the thickness) of the lower magnetic layer 10 (the fixed magnetic layer). The thickness of the fixed magnetic layer 44 is, for example, not less than 2 nm and not more than 6 nm.

The antiparallel coupling layer 45 causes antiparallel coupling between the magnetization of the lower magnetic layer 10 (the fixed magnetic layer) and the magnetization of the fixed magnetic layer 44. By this configuration, even in the case where the exchange coupling energy from the antiferromagnetic layer 42 is constant, the fixed magnetic field of the magnetization of the lower magnetic layer 10 (the fixed magnetic layer) can be strengthened. Accordingly, the effects on the magnetic noise for the sensor stacked body 50s can be reduced. The antiparallel coupling layer 45 may include, for example, Ru, Ir, and the like. The thickness of the antiparallel coupling layer 45 is, for example, not less than 0.8 nm and not more than 1 nm.

Figure 7C:
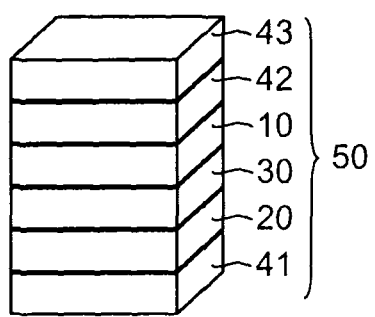

In the example shown in FIG. 7C, the foundation layer 41, the upper magnetic layer 20 (e.g., the free magnetic layer), the intermediate layer 30, the lower magnetic layer 10 (e.g., the fixed magnetic layer), the antiferromagnetic layer 42, and the protective layer 43 are stacked in this order. This configuration is called, for example, a top-type spin-valve film.

Figure 7D:
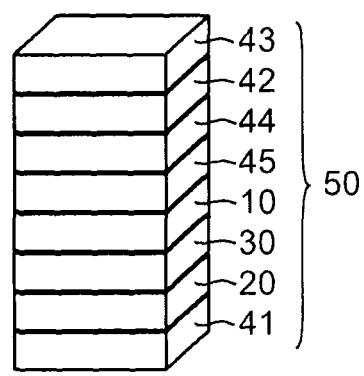

In the example shown in FIG. 7D, the foundation layer 41, the upper magnetic layer 20 (e.g., the free magnetic layer), the intermediate layer 30, the lower magnetic layer 10 (e.g., the fixed magnetic layer), the antiparallel coupling layer 45, the fixed magnetic layer 44, the antiferromagnetic layer 42, and the protective layer 43 are stacked in this order. This configuration is called, for example, a top-type synthetic spin-valve film.

Because the layers included in the top-type spin-valve film and the top-type synthetic spin-valve film are similar to the layers included in the bottom-type spin-valve film and the bottom-type synthetic spin-valve film, a description is omitted.

Interlayer coupling with the magnetization of the lower magnetic layer 10 may be used as a method to orient the magnetization of the upper magnetic layer 20 in a direction different from that of the tensile stress. The interlayer coupling acts to align the magnetization of the upper magnetic layer 20 to be parallel to the magnetization of the lower magnetic layer 10 at not more than 3 nm in the case where the intermediate layer 30 is a metal and at not more than 1.5 nm in the case where the intermediate layer 30 is an insulator. Accordingly, the magnetization of the upper magnetic layer 20 can be oriented in the same direction as the magnetization of the lower magnetic layer 10 by using a weak energy by fixing the magnetization of the lower magnetic layer 10 in a direction different from that of the tensile stress.

The magnetization of the upper magnetic layer 20 can be oriented in one direction by applying a magnetic field when forming the upper magnetic layer 20 (the free magnetic layer) using a sputtering apparatus. Because the magnetization is easily oriented in the direction of the magnetic field during the film formation, it is favorable to perform the film formation by sputtering while applying the magnetic field in a direction different from that of the tensile stress.

The embodiment uses such a sensor 50 that uses the spin. Thereby, it is possible to measure the pulse wave velocity for an extremely short distance.

According to investigations of the inventor of the application, in the case of measuring for an extremely short distance, for example, a position resolution of about several mm and 2 μs (microseconds) are necessary for the pulse wave velocity of a human body. From the two aspects of such a time resolution and position resolution, the capabilities of existing sensors are insufficient. In the embodiment, sufficient capability for the time resolution and the position resolution can be realized by the sensor 50 that uses the spin such as that recited above. For example, by using the sensor 50 according to the embodiment, a time resolution of about several hundred MHz is obtained. Because the position resolution is regulated by the element size such as those described above, the minimum position resolution of the sensor 50 is about 10 nm. Because the strain of the blood flow of the arterial vessel 210 is not actually measured directly but is measured by measuring the strain via the arterial vessel 210 and the skin 231, there are effects from such indirect materials. Therefore, even if the element size is reduced as much as possible, the element size in such a case is not the position resolution.

Figure 8:
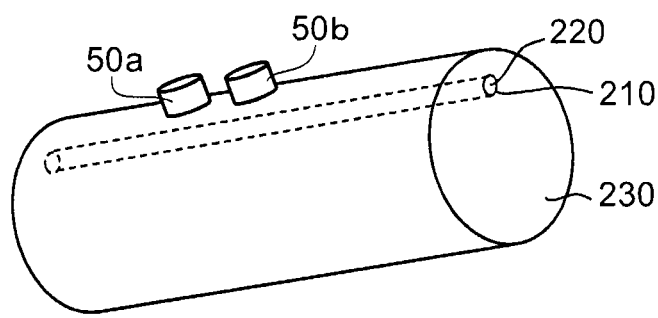
FIG. 8 is a schematic perspective view showing the operating state of the pulse wave velocity measuring device according to the first embodiment.

FIG. 8 is a schematic perspective view illustrating the operating state of the pulse wave velocity measuring device according to the first embodiment.

As shown in FIG. 8, the first sensor 50a and the second sensor 50b are disposed to oppose the arterial vessel 210 under the skin 231 of the body 230 of the examinee. The pulse wave of the blood 220 flowing through the arterial vessel 210 is sensed by the sensor 50.

Figure 9:
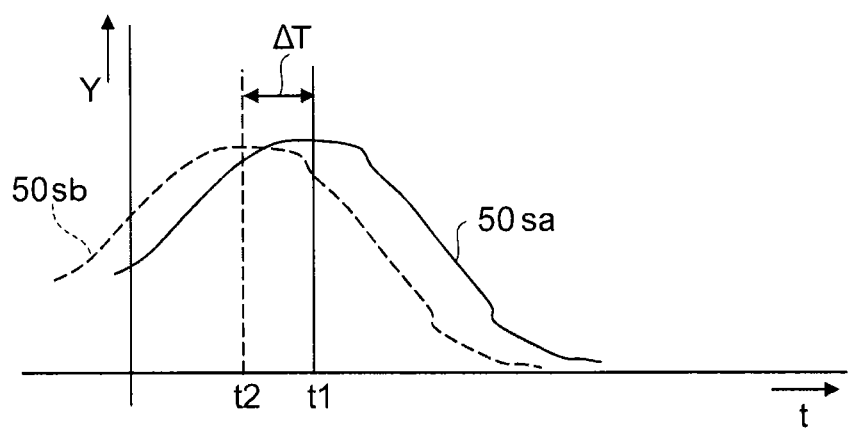
FIG. 9 is a graph showing the operation of the pulse wave velocity measuring device according to the first embodiment.

FIG. 9 is a graph illustrating the operation of the pulse wave velocity measuring device according to the first embodiment.

The horizontal axis of FIG. 9 is the time t. The vertical axis is a strain value Y sensed by the sensor 50.

For example, as shown in FIG. 9, a time t1 of, for example, the peak value of the first signal 50sa relating to the strain value Y obtained by the first sensor 50a is different from a time t2 of, for example, the peak value of the second signal 50sb relating to the strain value Y obtained by the second sensor 50b.

For example, the time of the sensing of the pulse wave by the first sensor 50a is taken to be the time t1. The time of the sensing of the pulse wave by the second sensor 50b is taken to be the time t2. The calculation unit 70 determines the interval between the time t1 and the time t2 (a signal propagation delay time ΔT between the sensors 50). The pulse wave velocity can be determined from the signal propagation delay time ΔT.

In the embodiment, it is possible to measure at substantially one location by measuring for an extremely short distance (e.g., the distance d between the sensors 50 being 1 cm and the like). Thereby, the complexity during the measurement is eliminated. On the other hand, the time difference of the detections of the pulse wave is exceedingly short when measuring for an extremely short distance. Therefore, the waveform of the first signal 50sa substantially matches the waveform of the second signal 50sb. For example, autocorrelation signal processing is performed to accurately calculate the pulse wave velocity from the first signal 50sa and the second signal 50sb. Thereby, the pulse wave velocity can be calculated accurately. The waveform of the first signal 50sa is substantially the same as the waveform of the second signal 50sb, and there is only a small temporal shift. By performing autocorrelation signal processing, the shift amount of such waveforms can be detected with high precision.

Figure 10:
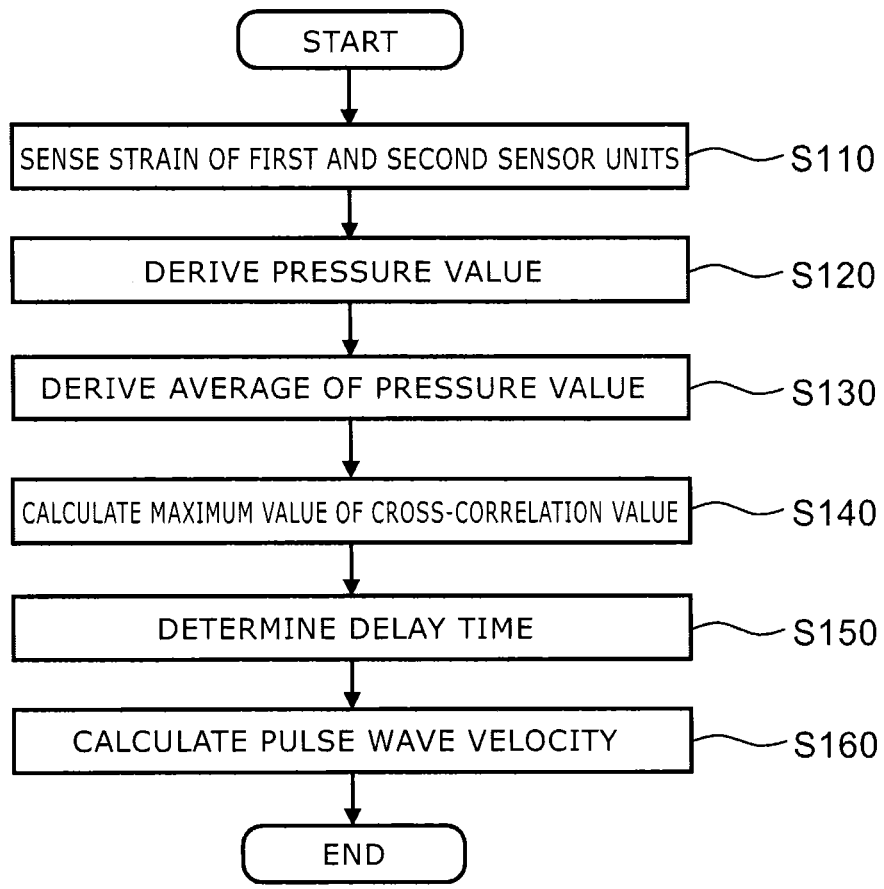
FIG. 10 is a flowchart showing operations of the pulse wave velocity measuring device according to the first embodiment.

FIG. 10 is a flowchart illustrating operations of the pulse wave velocity measuring device according to the first embodiment.

FIG. 10 shows an example of autocorrelation signal processing.

As shown in FIG. 10, the strain value Y corresponding to the pulse wave is sensed by the first sensor 50a and the second sensor 50b (step S110). In other words, the strain value Y of the sensor 50 is determined for the first measurement point (position=x) and the second measurement point (position=x+d). Specifically, a first strain value Y1 is determined for the first sensor 50a; and a second strain value Y2 is determined for the second sensor 50b.

From these results, the pressure values of these measurement points, i.e., a first pressure value P1(x) and a second pressure value P2(x+d), are derived (step S120).

$$P1(x) = aY1$$

$$P2(x+d) = aY2$$

Here, "a" is the transformation coefficient from the strain value to the pressure value. Generally, the calculation is a matrix calculation.

The blood pressure P is determined to be the average of the pressure values of the two points (the first pressure value P1(x) and the second pressure value P2(x+d)) (step S130).

In the case where only the blood flow velocity (the pulse wave velocity) is determined, the transformation to the pressure value may or may not be performed. In such a case, only the time delay is detected for the strain values Y that are obtained.

Regarding the time delay τ, a cross-correlation value I is calculated until the delay time ΔT can be identified. In other words, when comparing the first strain value Y1 and the second strain value Y2, the values are calculated for the time t being shifted to compare. The following formulas are the specific calculations at the respective times t with averaging.

$$I_{1,2,n}(\tau) = \frac{1}{T}\int_0^T Y_{1,n}(t)Y_{2,n}(t+\tau)\,dt \tag{1}$$

$$I_{1,2}(\tau) = \frac{1}{N}\sum_{n=1}^{N} I_{1,2,n}(\tau) \tag{2}$$

Here, N is the total number of measurements. The measurements are repeated until the arrival velocity of the signals from the measurement positions between the two points is determined, that is, until the τ at which $I_{1,2}(\tau)$ is largest is determined (step S140).

Then, τ obtained from this result is the delay time ΔT. In other words, the delay time ΔT is determined (step S150).

Then, a blood flow velocity (a pulse wave velocity) V is determined by calculating from d/ΔT (step S160).

Figure 11:
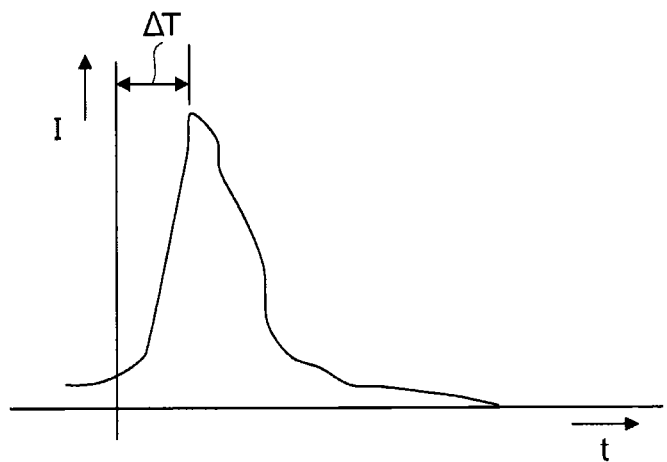
FIG. 11 is a graph showing the operation of the pulse wave velocity measuring device according to the first embodiment.

FIG. 11 is a graph illustrating the operation of the pulse wave velocity measuring device according to the first embodiment.

The horizontal axis of FIG. 11 is the time t. On the vertical axis, the strain values Y (the first strain value Y1 and the second strain value Y2) of the first signal 50sa and the second signal 50sb are determined. This is the first cross-correlation value I.

Thus, the cross-correlation value I is a maximum when the shifted time t is the delay time ΔT. Thus, the delay time ΔT can be determined.

For example, such a cross-correlation can be implemented by the calculation unit 70. In other words, the derivation of the difference of the times of the sensing by the calculation unit 70 may include autocorrelation signal processing of the signal (the first signal 50sa) of the sensing of the pulse wave by the first sensor 50a and the signal (the second signal 50sb) of the sensing of the pulse wave by the second sensor 50b.

Figure 12:
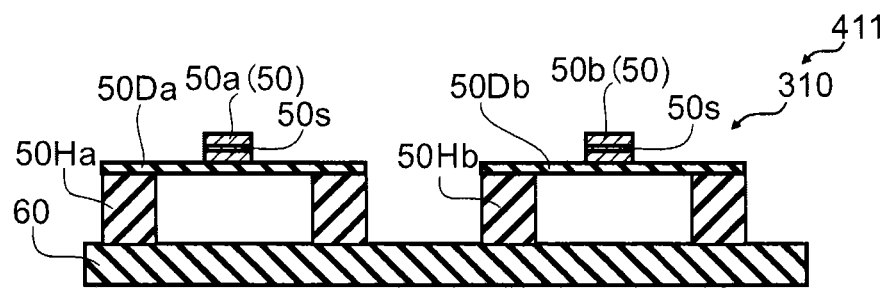
FIG. 12 is a schematic cross-sectional view showing another pulse wave velocity measuring device according to the first embodiment.

FIG. 12 is a schematic cross-sectional view illustrating the configuration of another pulse wave velocity measuring device according to the first embodiment.

This drawing illustrates only a portion of the measurement sensor 310; and the calculation unit 70 is not illustrated.

In the pulse wave velocity measuring device 411 according to the embodiment as shown in FIG. 12, the first sensor 50a and the second sensor 50b further include diaphragms. Namely, the first sensor 50a includes a first diaphragm 50Da connected to the sensor stacked body 50s of the first sensor 50a. The second sensor 50b includes a second diaphragm 50Db connected to the sensor stacked body 50s of the second sensor 50b.

In this example, the first diaphragm 50Da is provided on a first support body 50Ha that is provided on the base body

60. The second diaphragm 50Db is provided on a second support body 50Hb that is provided on the base body 60. The first diaphragm 50Da and the second diaphragm 50Db can move while being separated from the base body 60. Thereby, the pulse wave can be received via pressure; and the sensitivity of the sensing improves.

Figure 13:
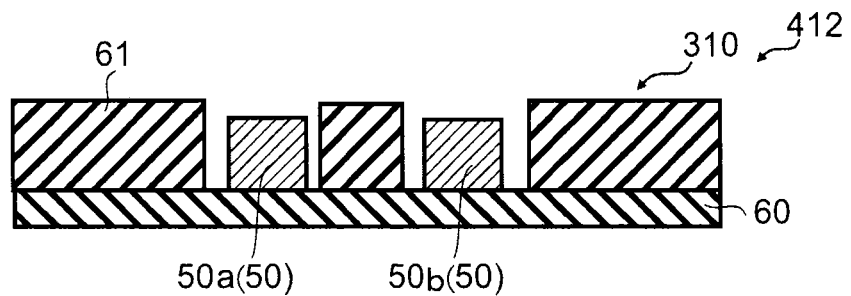
FIG. 13 is a schematic cross-sectional view showing another pulse wave velocity measuring device according to the first embodiment.

FIG. 13 is a schematic cross-sectional view illustrating the configuration of another pulse wave velocity measuring device according to the first embodiment.

This drawing illustrates only a portion of the measurement sensor 310; and the calculation unit 70 is not illustrated.

In the pulse wave velocity measuring device 412 according to the embodiment as shown in FIG. 13, the base body 60 includes an adhesive layer 61. The measurement sensor 310 is fixed to the body 230 of the examinee by the adhesive layer 61. Thereby, the measurement sensor 310 is more convenient.

Figure 14:
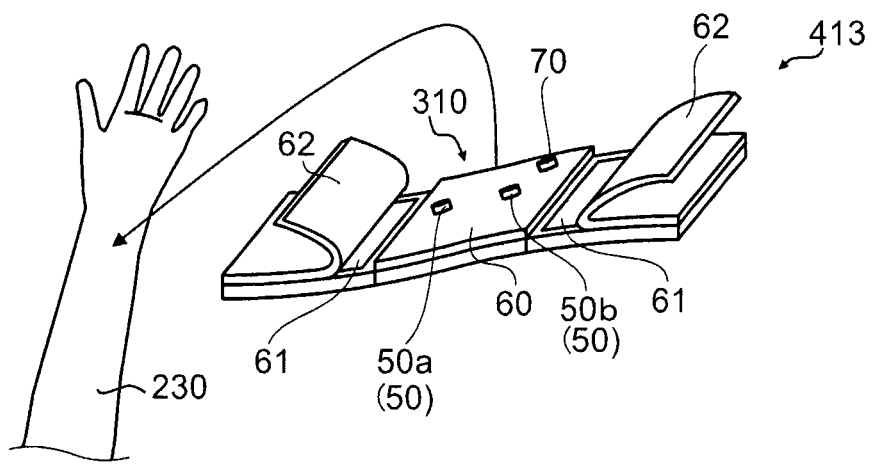
FIG. 14 is a schematic view showing another pulse wave velocity measuring device according to the first embodiment.

FIG. 14 is a schematic view illustrating the configuration of another pulse wave velocity measuring device according to the first embodiment.

In the pulse wave velocity measuring device 413 according to the embodiment as shown in FIG. 14, a soft film is used as the base body 60. Two or more sensors 50 are provided on the film. In this example, the calculation unit 70 is provided proximally to the sensors 50. The adhesive layer 61 is provided on the film around the sensors 50 and the calculation unit 70. Before using the pulse wave velocity measuring device 413, the adhesive layer 61 is covered with a separator film 62. When using, the separator film 62 is peeled; and the pulse wave velocity measuring device 413 is adhered to the body 230 by the adhesive layer 61. By using the soft film as the base body 60, the discomfort felt by the user is reduced. For example, the pulse wave velocity measuring device 413 can be adhered to the body 230 as an adhesive bandage. Thereby, continuous measurement in daily life becomes easier. In this example, the calculation unit 70 may be provided separately from the base body 60.

FIG. 15A to FIG. 15D are schematic views illustrating the configuration and the state of use of another pulse wave velocity measuring device according to the first embodiment.

Figure 15A:
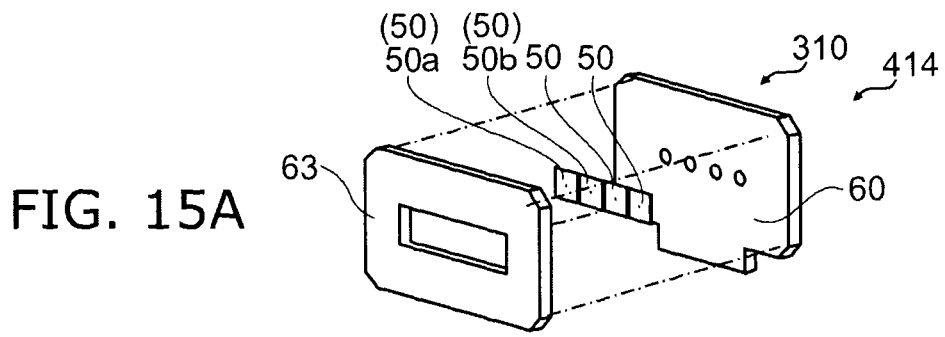
FIG. 15A to FIG. 15D are schematic views showing the configuration and the state of use of another pulse wave velocity measuring device according to the first embodiment.
Figure 15B:
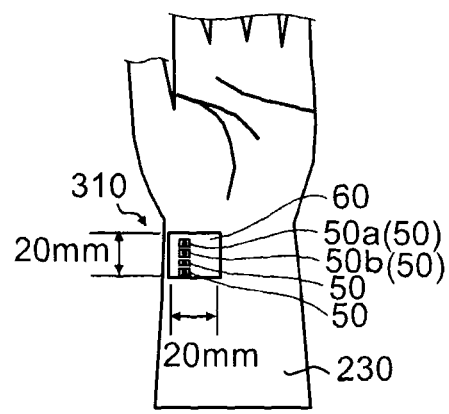
Figure 15C:
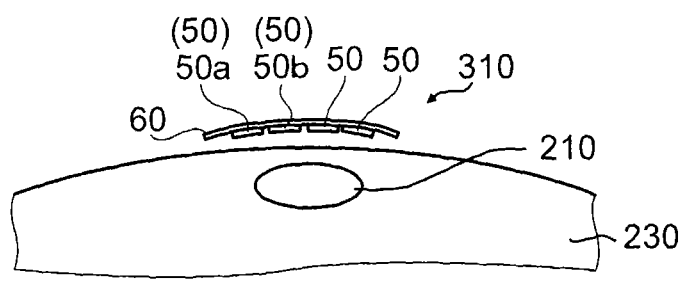
Figure 15D:
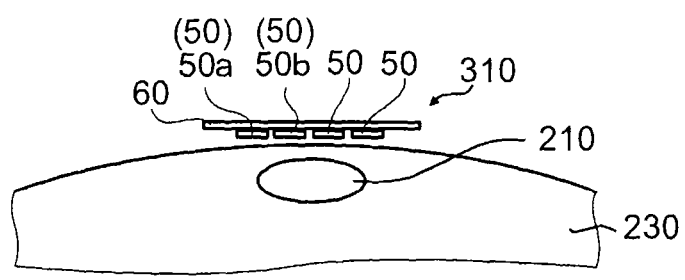

FIG. 15A is a schematic exploded perspective view illustrating the configuration of the pulse wave velocity measuring device 414 according to the embodiment. FIG. 15B is a schematic view illustrating the state of use of the pulse wave velocity measuring device 414. FIG. 15C and FIG. 15D are schematic cross-sectional views illustrating states of use of the pulse wave velocity measuring device 414.

As shown in FIG. 15A, the pulse wave velocity measuring device 413 includes four sensors 50. For example, there are cases where it is difficult for one sensor 50 to sense the pulse wave of the arterial vessel 210 because, for example, a discrepancy occurs when adhering the measurement sensor 310 to the body 230 or the like. By providing three or more sensors 50 in such a case, it becomes easier to implement the desired operation even in such a case because the pulse wave can be sensed by the other sensors 50.

In this example, a spacer 63 is provided around the sensors 50. The spacer 63 is made of, for example, soft rubber with a thickness of, for example, about 0.5 mm. By providing such a spacer 63, the discomfort felt by the user can be reduced. The spacer 63 is provided if necessary and may be omitted.

As shown in FIG. 15B, the measurement sensor 310 is adhered to the body 230 (e.g., the wrist or the like). The size of the measurement sensor 310 is, for example, about 20 mm by about 20 mm.

In the case where the base body 60 is soft as shown in FIG. 15C, the base body 60 bends along the configuration of the body 230 (e.g., the wrist). However, in the case where the rigidity of the base body 60 is relatively high as shown in FIG. 15D, the base body 60 may maintain a substantially planar configuration.

Figure 16:
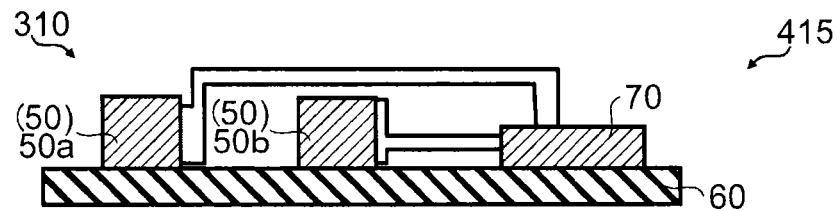
FIG. 16 is a schematic cross-sectional view showing another pulse wave velocity measuring device according to the first embodiment.

FIG. 16 is a schematic cross-sectional view illustrating the configuration of another pulse wave velocity measuring device according to the first embodiment.

In the pulse wave velocity measuring device 415 according to the embodiment as shown in FIG. 16, the calculation unit 70 is provided on the base body 60. Thereby, the device can be downsized further and becomes more convenient.

Second Embodiment

The embodiment relates to a pulse wave velocity measurement method.

Figure 17:
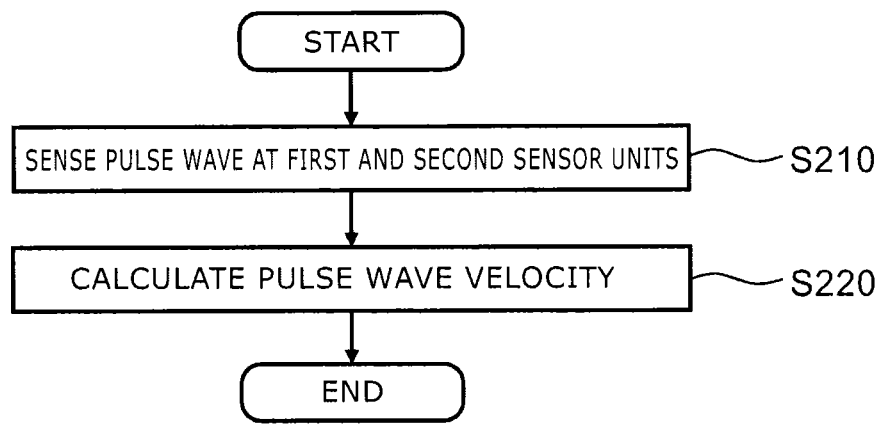
FIG. 17 is a flowchart showing the pulse wave velocity measurement method according to a second embodiment.

FIG. 17 is a flowchart illustrating a pulse wave velocity measurement method according to a second embodiment.

As shown in FIG. 17, the measurement method senses a pulse wave propagating through the interior of a vessel (e.g., the arterial vessel 210) of a sense object by causing the measurement sensor 310 including the base body 60, the first sensor 50a, and the second sensor 50b to contact the sense object to sense the pulse wave using the first sensor 50a and the second sensor 50b, where the first sensor 50a is held by the base body 60, and the second sensor 50b is held by the base body 60 such that the distance between the first sensor 50a and the second sensor 50b is regulated by the base body 60 (step S210).

The measurement method derives the pulse wave velocity based on the difference between the time t1 of the sensing of the pulse wave by the first sensor 50a and the time t2 of the sensing of the pulse wave by the second sensor 50b (step S220).

For example, the processing described in regard to FIG. 10 is implemented.

Thereby, a pulse wave velocity measurement method that can measure the pulse wave velocity in a local measurement range can be provided.

In the first and second embodiments recited above, the sensors 50 sense a pulse wave propagating through the interior of a vessel. Although the case is described in the examples recited above where this vessel is a blood vessel, the embodiments are not limited thereto. For example, the sensors 50 may sense the pulse wave propagating through the interior of a lymph vessel. The embodiments can be applied to any vessel of an organism (animals, plants, and the like) in which a pulse wave is transmitted. Also, the embodiments can be applied to any vessel provided in an inanimate object in which a pulse wave is transmitted.

According to the embodiments, a pulse wave velocity measuring device and a pulse wave velocity measurement method that can measure the pulse wave velocity in a local measurement range are provided.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in pulse wave velocity measuring devices such as first sensors, second sensors, base bodies, calculation units, first to fourth ferromagnetic layers, first and second intermediate layers, diaphragms, adhesive layers, and the like from known art; and such practice is included in the scope of the invention to the extent that similar effects are obtained.

Further, any two or more components of the specific examples may be combined within the extent of technical feasibility and are included in the scope of the invention to the extent that the purport of the invention is included.

Moreover, all pulse wave velocity measuring devices and pulse wave velocity measurement methods practicable by an appropriate design modification by one skilled in the art based on the pulse wave velocity measuring devices and the pulse wave velocity measurement methods described above as embodiments of the invention also are within the scope of the invention to the extent that the spirit of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A pulse wave velocity measuring device, comprising:
    a base body;
    a first support body provided on the base body;
    a first diaphragm supported by the first support body to be separated from the base body;
    a first sensor provided on a part of a first upper surface of the first diaphragm to sense a pulse wave propagating through an interior of a vessel, the part of the first upper surface overlapping the first sensor and a first cavity in a first direction perpendicular to the first upper surface, the first cavity being provided under the first diaphragm, an other part of the first upper surface not overlapping the first sensor in the first direction and overlapping the first cavity in the first direction;
    a second support body provided on the base body;
    a second diaphragm supported by the second support body to be separated from the base body and separated from the first diaphragm;
    a second sensor provided on a part of a second upper surface of the second diaphragm to sense the pulse wave, the part of the second upper surface overlapping the second sensor and a second cavity in a second direction perpendicular to the second upper surface, the second cavity being provided under the second diaphragm, an other part of the second upper surface not overlapping the second sensor in the second direction and overlapping the second cavity in the second direction; and
    a calculation unit configured to derive a difference between a time of the sensing of the pulse wave by the first sensor and a time of the sensing of the pulse wave by the second sensor, the first sensor includes a first ferromagnetic layer, a second ferromagnetic layer, and a first intermediate layer provided between the first ferromagnetic layer and the second ferromagnetic layer, the first intermediate layer being nonmagnetic,
    the second sensor includes a third ferromagnetic layer, a fourth ferromagnetic layer, and a second intermediate layer provided between the third ferromagnetic layer and the fourth ferromagnetic layer, the second intermediate layer being nonmagnetic,
    wherein
    a first electrical resistance between the first ferromagnetic layer and the second ferromagnetic layer changes depending on a change of a first magnetization direction of the first ferromagnetic layer based on inverse magnetostrictive effect corresponding to a first stress applied to the first ferromagnetic layer from the first diaphragm deforming depending on the pulse wave, and
    a second electrical resistance between the third ferromagnetic layer and the fourth ferromagnetic layer changes depending on a change of a third magnetization direction of the third ferromagnetic layer based on inverse magnetostrictive effect corresponding to a second stress applied to the third ferromagnetic layer from the second diaphragm deforming depending on the pulse wave.

2. The device according to claim 1, wherein the first intermediate layer and the second intermediate layer include at least one of Cu, Au and Ag, and a thickness of the first intermediate layer and a thickness of the second intermediate layer are not less than 1 nanometer and not more than 7 nanometers.

3. The device according to claim 1, wherein the first intermediate layer and the second intermediate layer include at least one of a magnesium oxide, aluminum oxide, titanium oxide and zinc oxide, and a thickness of the first intermediate layer and a thickness of the second intermediate layer are not less than 0.6 nanometers and not more than 2.5 nanometers.

4. The device according to claim 1, wherein the base body includes an adhesive layer.

5. The device according to claim 1, wherein the calculation unit is provided on the base body.

6. The device according to claim 1, wherein the deriving of the difference by the calculation unit includes autocorrelation signal processing of a signal of the sensing of the pulse wave by the first sensor and a signal of the sensing of the pulse wave by the second sensor.

7. The device according to claim 1, wherein the base body includes at least one of a silicon substrate and a printed circuit board.

8. The device according to claim 1, wherein the base body includes a plastic substrate.

9. The device according to claim 1, wherein the base body is flexible.

10. The device according to claim 1, wherein the distance is not less than 1 mm and not more than 5 cm.

11. The device according to claim 1, wherein the distance is not less than 5 mm and not more than 2 cm.

12. The device according to claim 1, wherein a size of the first sensor and the second sensor is not less than 100 nm×100 nm and not more than 10 μm×10 μm.

* * * * *